United States Patent [19]

Ivanics et al.

[11] Patent Number: 5,466,833
[45] Date of Patent: Nov. 14, 1995

[54] PROCESS FOR THE PREPARATION OF 13,14-DIHYDRO-15(R)-17-PHENYL-18,19,20-TRINOR-PGF$_{2\alpha}$ ISOPROPYL ESTER

[75] Inventors: József Ivanics; Tibor Szabó; István Hermecz; Gyula Dalmadi; Józsefné Ivanics; Gáborné Kovács, all of Budapest, Hungary; Resul Bahram, Uppsala, Sweden

[73] Assignees: Kabi Pharmacia AB, Uppsala, Sweden; Chinoin Ltd., Budapest, Hungary

[21] Appl. No.: 319,327

[22] Filed: Oct. 6, 1994

Related U.S. Application Data

[63] Continuation of Ser. No. 30,440, filed as PCT/HU92/00025, Jun. 19, 1992, abandoned.

[30] Foreign Application Priority Data

Jun. 24, 1991 [HU] Hungary ................. 2092/91

[51] Int. Cl.$^6$ ................. C07D 307/02
[52] U.S. Cl. ............. 549/475; 562/470; 560/60
[58] Field of Search ............ 549/475; 560/60; 562/470

[56] References Cited

FOREIGN PATENT DOCUMENTS 2234709  2/1973  Germany.
90/02553  3/1990  WIPO.

*Primary Examiner*—Paul J. Killos
*Attorney, Agent, or Firm*—Herbert Dubno; Jonathan Myers

[57] ABSTRACT

The invention relates to a novel process for the preparation of 13,14-dihydro-15 (R)-17-phenyl-18,19,20-trinor-PGF$_{2\alpha}$ isopropyl ester of the formula (I)—wherein R stands for saturated or unsaturated straight, branched or cyclic $C_{1-7}$ alkyl or phenyl or benzyl group—

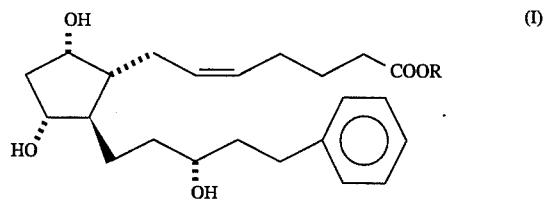

(I)

8 Claims, No Drawings

PROCESS FOR THE PREPARATION OF 13,14-DIHYDRO-15(R)-17-PHENYL-18,19,20-TRINOR-PGF$_{2\alpha}$ ISOPROPYL ESTER This is a continuation of application Ser. No. 08/030,440 filed as PCT/HU92/00025 on Jun. 19, 1992, now abandoned.

FIELD OF THE INVENTION

This invention relates to a novel process for the preparation of 13,14-dihydro-15(R)-17-phenyl-18,19,20-trinor-PGF$_{2\alpha}$ esters of the general formula (I)

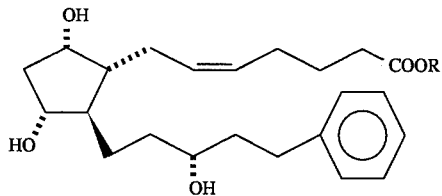

(I)

wherein R stands for saturated or unsaturated straight, branched or cyclic C$_{1-7}$ alkyl or phenyl or benzyl group.

It is known that many prostaglandin derivatives are capable to decrease intraocular tension when used topically, i.e. they are useful for the treatment of glaucoma (published European patent applications Nos. 0,170,258 and 0,253, 094). Prostaglandin derivatives possessing particulary advantageous effect have been described in the published PCT patent application No. WO 90/02553. From these, the compound of formula (I) has proved to be particularly favorable. A method for synthesis of the compound of formula (I) has been disclosed in the PCT application cited above.

OBJECT OF THE INVENTION

The object of this invention is to provide an improved method for a synthesis, which is useful for the production of the compound of formula (I) in a good yield, in large amounts, with the desired purity.

DESCRIPTION OF THE INVENTION

It has been found that the compound of formula (I) is obtained in a high purity and in high yield by reducing the oxo group on the side chain of the compound of formula (VII),

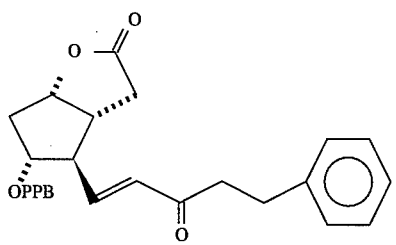

(VII)

transforming the obtained compound of the formula (VI)

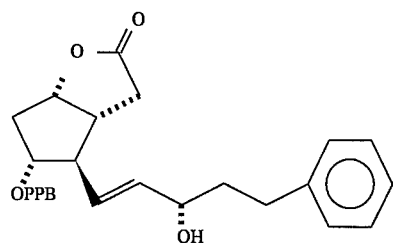

(VI)

by hydrogenation to 3,3a,4,5,6,6a-hexahydro-2-oxo-4-[5'-phenyl-3'(R)-hydroxy-1'-pentyl]-5-(4'-phenylbenzoyloxy)-2H-cyclopenta[b]furan of the formula (V)

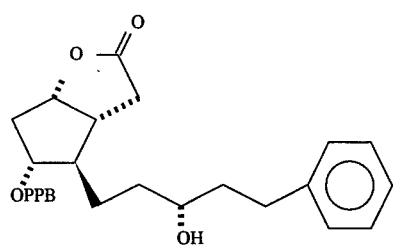

(V)

reducing the compound of formula (V) to 3,3a,4,5,6,6a-hexahydro-2-hydroxy-4-[5'-phenyl-3'(R)-hydroxy-1'-pentyl]-5-(4'-phenylbenzoyloxy)-2H-cyclopenta[b]furan of the formula (IV),

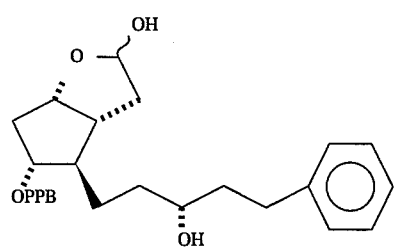

(IV)

removing the protective group from the compound of formula (IV) to obtain 3,3a, 4,5,6,6a-hexahydro-2,5-dihydroxy-4-[5'-phenyl-3'(R)-hydroxy-1'-pentyl]-2H-cyclopenta[b]furan of the formula (III)

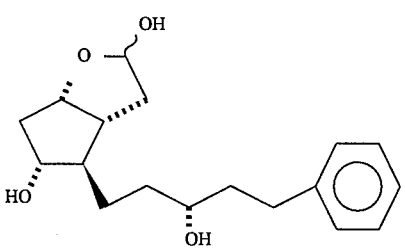

(III)

then transforming the compound of formula (III) to give the compound of the formula (II)

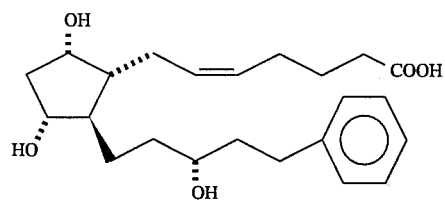

(II)

by using 4-carboxybutyl-triphenylphosphonium halide and finally, transforming the compound of formula (II) with a compound of the general formula R-X, wherein R has the same meaning as stated above, X is halogen, sulphate, mesyl, tosyl or any other suitable group, to 13,14-dihydro-15(R)17-phenyl-18,19,20-trinor-PGF$_{2\alpha}$ ester of the general formula (I).

The compound of formula (VII) is prepared from phenylphosphonium salts and 3,3a, 4,5,6,6a-hexahydro-2-oxo-4-(5'-phenyl-3-oxopent-1'-enyl)-5-(4'-phenylbenzoyloxy)-2H-cyclopenta [b]furan, which is a known prostaglandin intermediate and can be obtained e.g. according to the U.S. Pat. No. 3,778,450. Other reagents used are commercially available.

The reduction of the compound of formula (VII) to the compound of formula (VI) is carried out by using any reagent known suitable for the reduction of enones especially from the chemical literature of prostaglandins, e.g. by using lithium tri(sec-butyl)borohydride or sodium borohydride [J. Am. Chem. Soc. 94, 8616 (1972); J. Am. Chem. Soc. 106, 6717 (1984)]. The transformation of the compound of formula (VI) to the substances of formula (V) may be realized in the presence of a catalyst commonly used for hydrogenation, for example palladium on carbon or rhodium on carbon but preferably palladium on carbon, preferably in the presence of a base or sodium salts like sodium hydroxide or sodium nitrite.

The transformation of the compound of formula (III) to a compound of formula (II) may be carried out by using any combination of conditions (base, solvent and the like) commonly used in the Wittig reaction. Preferably sodium amide, potassium tertbutylate, sodium hydride or butyl lithium as a base and diglyme, DMSO, DMF or tetrahydrofurane as a solvent can be used. The transformation of the compound of formula (V) to the compound of formula (IV) and subsequently, the transformation of the compound of formula (IV) to the product of formula (III) can be achieved without isolating the compound of formula (IV), too, under suitably selected conditions. It is obvious to a man skilled in the art that the compounds of the formula (II–VII) and the general formula (I) may contain further substituents and the claimed process still takes place. Such reactions are therefore clearly within the scope of this patent application.

We summarize our process on the following Scheme I.

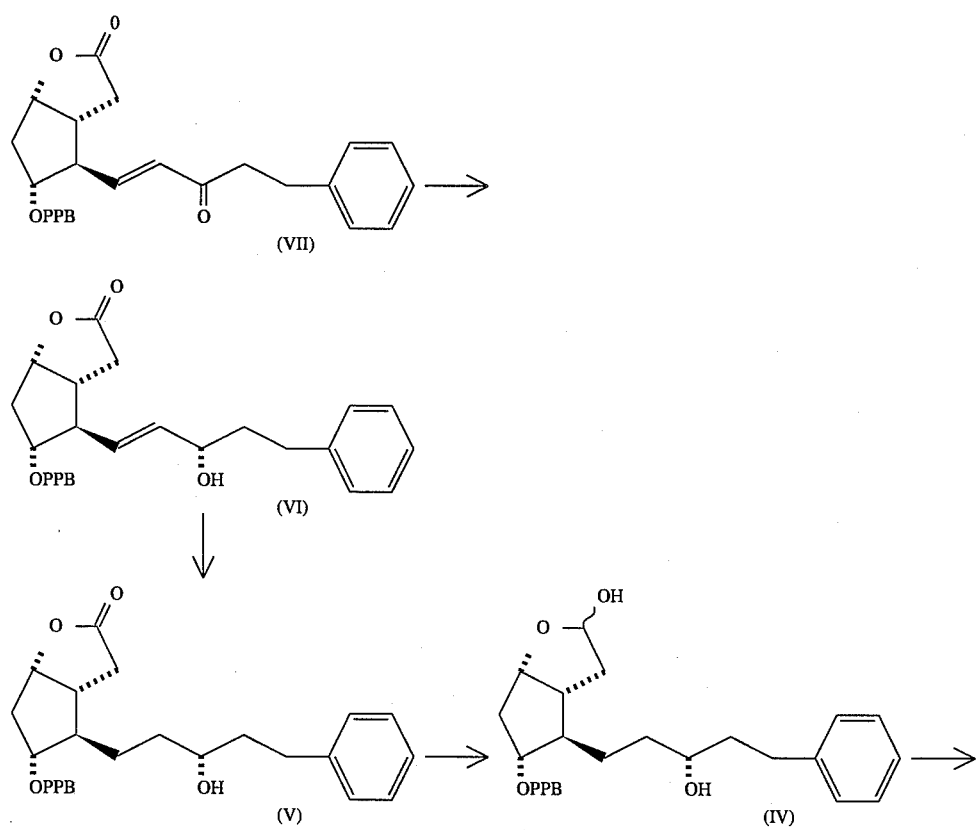

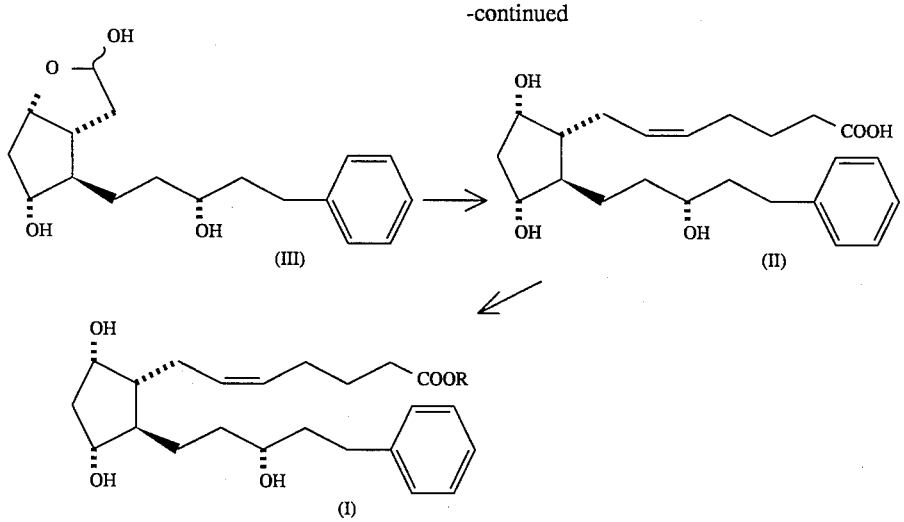

-continued

The process of the invention is illustrated in detail by the following non-limiting Examples.

EXAMPLE 1

Preparation of 3,3a, 4,5,6,6a-hexahydro-2-oxo-4-(5'-phenyl-3-oxo-pent-1'-enyl)-5-(4'-phenylbenzoyloxy)-2H-cyclopenta[b]furan [compound of the formula (VII)]

A solution containing 3,3a, 4,5,6,6a-hexahydro-2-oxo-4-hydroxymethyl-5-(4'-phenylbenzoyloxy)-2H-cyclopenta[b]furan (18 g, 51 mmol) in dry toluene (110 ml) is cooled to 18° C., then the solution of dicyclohexylcarbodiimide (18 g, 83 mmol) and 1 Molar phosphoric acid solution (8 ml, 8 mmol) in dry dimethylsulfoxide is added. The reaction mixture is maintained below a temperature of 25° C. under continuous cooling. After 30 minutes, the following reagents are added to the reaction mixture in intervals of 30 minutes:

1M phosphoric acid solution (4 ml) in dimethylsulfoxide; dicyclohexylcarbodiimide (9 g, 41 mmol) and 1M phosphoric acid solution (5 ml) in dimethylsulfoxide.

Subsequently, the reaction mixture is stirred at 20°–22° C. for 2 hours. Meanwhile triphenyl-(4-phenyl-3-oxobutyl)phosphonium iodide (27.3 g, 50 mmol) and 5M calcium hydroxide solution (10 ml) in toluene (250 ml) are stirred at 45° C. for 90 minutes; then the solution obtained is washed 3 times with 100 ml of water each of 45°–50° C. temperature, until neutral, then toluene (45 ml) are removed from the solution under reduced pressure. The residual solution is added to the other reaction mixture at a rate that its temperature does not exceed 30° C. After 2 hours the solution is heated to 35° C., after an additional hour concentrated hydrochloric acid (4 ml) dissolved in water (30 ml) is added and then stirred for 1 additional hour. The precipitate is removed by filtration, the filtrate is washed with toluene and after combination, the toluene solution is washed with water (150 ml), 4 times with saline (30 ml), dried over anhydrous sodium sulfate and then evaporated to 350 ml.

The above solution is transferred to a column containing silica gel (135 g) and toluene and eluted by using an 5:1 mixture of toluene and ethyl acetate. After evaporating the solution, dark brown solid (21 g) are obtained which is dissolved in boiling methanol (840 ml). After cooling the solution to 0° C., filtering the precipitate and washing with cold methanol (30 ml), the product is dried at room temperature to give the title product of formula (VII) as a white substance in a yield of 12.0 g (48.7%), m.p.: 129°–130° C., $[\alpha]_D = -145°$ (c=1, ethyl acetate).

EXAMPLE 2

Preparation of 3,3a, 4,5,6,6a-hexahydro-2-oxo-4-(5'-phenyl-3-oxo-pent-1'-enyl)-5-(4'-phenylbenzoyloxy)-2H-cyclopenta[b]furan [compound of the formula (VII)]

a) To a solution of 3,3a, 4,5,6,6a-hexahydro-2-oxo-4-hydroxymethyl-5-(4'-phenylbenzoyloxy)-2H-cyclopenta[a]furan (27 kg) in toluene (165 L), cooled to 17° C., dicyclohexylcarbodiimide (DCC) (27 kg), phosphoric acid in dimethylsulfoxid (DMSO) 1M (12 L) was added. The temperature of the reaction mixture was kept below 25° C. after 60 min. The following reagents in the following orders were added to the reaction mixture in 60 min. intervals; phosphoric acid in DMSO 1M (6 L), DCC (13.5 kg), phosphoric acid in DMSO 1M (6 L). The reaction mixture was stirred at 20°–25° C. for an additional 7 hours (TLC monitoring). TLC Rf=0.32 (silicagel, AcOEt:toluene) (silicagel, toluene-AcOEt-AcOH: 30:15:2)

b) Triphenyl-2-oxo-4-phenylbutylphosphonium iodide (38.4 kg), potassium hydroxide (5 kg) in water (105 L), toluene (210 L) and dichloromethane (90 L) was stirred vigorously for 3 hours followed by addition of sodium chloride (5 kg). The organic layer was separated and washed with brine (3×113 L), dried on sodium sulphate, concentrated in vacuo to 70 L, this solution was added to the solution prepared by the method described in part a) of this example at a rate that the temperature of the reaction mixture not exceed 25° C. After 7 hours the solution was cooled to 18° C. (TLC monitoring). A solution of concentrated HCl (6 L) in water (45 L) was added and the mixture was stirred for an hour. The precipitate was removed by filtration, washed with toluene (2×45 L+2×23 L). The organic layer was washed with water (225 L) and brine (4×45 L), the water solution was extracted with toluene (2×23+1×30 L), the organic layers were collected and dried on sodium sulphate (15 kg), filtered, washed with toluene (2×15 L), and evaporated in vacuo to 85 L and added methanol (240 L), cooled to 0° C., filtered, washed with methanol:toluene 9:1 (49 L) and methanol (98+60 L) to give a white crystalline product, mp: 129°–130° C., (yield 19.4 kg, 52.7%), $[\alpha]_D^{20}=-116(c=1.26, CH_3CN)$.

EXAMPLE 3

Preparation of the compound of the formula (VI)

A mixture containing 1.04M lithium-tri(sec-butyl)borohydride (418 ml, 0,434 mol) in tetrahydrofuran solution and dry diethyl ether (420 ml) is cooled to −130° C. The compound of formula (VII) (200 g) are dissolved in tetrahydrofuran (1000 ml) and diethyl ether (900 ml), cooled to −130° C. and added to the above borohydride solution during 1 minute. After 5 minutes the reaction mixture is poured into a mixture containing water (5.5 l), 2M sodium sulfate solution (250 ml) and saline (500 ml) and stirred at room temperature for 15 minutes. The solution is successively washed with water (2 L), ethyl acetate (1 L) and twice with saline (200 ml) each, dried over anhydrous sodium sulfate and evaporated under reduced pressure. The liquid residue obtained is transferred to a column containing silica gel (5 kg). After eluting with a 7:1 mixture containing methylene chloride and ethyl acetate and recrystallizing the product obtained from the mixture of ethyl acetate (80 ml), diisopropyl ether (160 ml) and hexane (80 ml), white, crystalline title compound of formula (VI) (69.7 g) are obtained, m.p.: 129°–130° C., $[\alpha]_D=-108°$ (c=1, ethyl acetate).

EXAMPLE 4

Preparation of the compound of the formula (VI)

To a stirred suspension of enone of the formula (VII) (19.3 kg) in methanol (4.5 L) and chloroform (200 L), cooled to −3°–5° C. sodium borohydride (2.38 kg) was added (TLC monitoring). The reaction mixture was poured into water (20 L) followed by addition of conc. HCl (12.6 L). The mixture was dried on Silicagel (30 kg), filtered, washed with chloroform (60+30 L). The organic layer was concentrated to 60 L and chromatographed on two columns. Both columns were packed with silicagel (135 kg) and toluene (300 L). Toluene: AcOEt 666 L:133 L+(250 L:150 L) and AcOEt 250 L were used successively as eluent, for both columns. Fraction V (410 L) was concentrated in vacuo to 35 L. To the residue diisopropyl ether (90 L) was added, cooled to 0° C./−5° C., stirred for an hour. The white crystalline product was filered and washed with DIPE-AcOEt 3:1 (16 L). Yield 7.38 kg (38%). TLC:Rf=0.5 (silicagel; AcOEt) (0.36 (AcOEt:hexane 1:1) $[\alpha]=-101.59$ (c=0.69 $CH_3CN$).

EXAMPLE 5

Preparation of 3,3a, 4,5,6,6a-hexahydro-2-oxo-4-[5'-phenyl-3'(R)-hydroxy-1'-pentyl]-5-(4'-phenyl-benzoyloxy)-2H-cyclopenta [b]furan[compound of the formula (V)]

To a solution containing the compound Formula (VI) (70 g, 144 mmol) in ethanol (2 L) at 18°–20° C., palladium-on-carbon catalyst (7.0 g) and sodium nitrite (3.5 g, 50 mmol) as a suspension in water (100 ml) are added. The mixture is stirred under hydrogen of 5 bar pressure for 90 minutes, then the catalyst is filtered off, 1M hydrochloric acid solution (100 ml) are added and the mixture is stirred at room temperature for 1 hour. After removing the solvent under reduced pressure the oily residue obtained is dissolved in ethyl acetate (700 ml). The aqueous phase is twice extracted with ethyl acetate (200 ml) each and the combined ethyl acetate solution is twice washed with saline (100 ml) each. After drying over anhydrous sodium sulfate and evaporating the solvent, the title compound of formula (V) is obtained as an oily residue in a yield of 95% with an $R_f$ value of 0.23 (developing system hexan/ethyl acetate 1:1), $[\alpha]_D=-66°$ (c=1, ethyl acetate). IR spectrum (taken on a Zeiss Specord M-80 type spectrometer) (KBr, cm$^{-1}$): 3500 (OH), 3080, 3020 (CH aromatic), 2940, 2860 (CH aliphatic), 1770, 1710 (C=O), 1610, 1500 (aromatic ring vibration), 1290, 1190, 1100 (C—O—C), 850 (p-subst. aromatic), 750, 700 (monosubst. aromatic).

EXAMPLE 6

Preparation of 3,3a, 4,5,6, 6a-hexahydro-2-oxo-4-[5'-phenyl-3'(R)-hydroxy-1'-pentyl]-5-(4'-phenyl-benzoyloxy)-2H-cyclopenta[b]furan [compound of the formula (V)]

To a solution of the compound of the formula (VI) (7.2 kg) in ethanol abs. (200 L) at 15°–20° C. a suspension of 10% Pd/C (1.4 kg) and sodium nitrite (0.72 kg) in water (36 L) was added. The solution was stirred under hydrogen atmosphere (1200 kbL) for 3 hrs (TLC monitoring). 2M HCl (105 L) was added and stirred at room temperature for 1 hour. The catalyst was removed by filtration, washed with ethanol abs. (20 L). The solvent was removed in vacuo to 50 L. The resulting oil was dissolved in toluene (140 L), washed with brine 15% (3×30 L). The water phase was washed with toluene (20L). The combined organic extracts were dried on sodium sulphate (10 kg) and sodium hydrogen carbonate (0.5 kg), respectively, filtered. The precipitate was washed with toluene (30 L). The solvent was removed in vacuo to have a residue (90 L) which was used directly for the next step. The residue contains the compound of the formula (V) (7.03 kg, 96.7%).

EXAMPLE 7

Preparation of 3,3a, 4,5,6,6a-hexahydro-2-hydroxy-4-[5'-phenyl-3'(R)-hydroxy-1'-pentyl]-5-(4'-phenyl-benzoyloxy)-2H-cyclopenta [b]furan [compound of the formula (IV)]

After dissolving 3,3a, 4,5,6,6a-hexahydro-2-oxo-4-[5'-phenyl-3'(R)-hydroxy-1'-pentyl]-5-(4'-phenylbenzoyloxy)-2H-cyclopenta[b]furan (65.7 g, 135 mmol) in dry tetrahydrofuran (330 ml), diisobutyl Aluminum hydride (150 ml, 297 mmol) in dry hexane solution (150 ml) are dropwise added at a temperature between −65° C. and −75° C. After stirring the reaction mixture for 10 minutes, the solution is poured into the mixture of water (1 L) and 2M sodium hydrogen sulfate solution (500 ml) and stirred for 30 minutes. The solution is washed with ethyl acetate (1 liter and than twice with 500 ml) each, then the combined organic phase is twice washed with saline (200 ml) each. After evaporating the organic phase under reduced pressure, the title product of formula (IV) is obtained as a colorless oily residue which is used without purification in the next step, $R_f=0.25$ (benzene/ethyl acetate 1:1).

EXAMPLE 8

Preparation of 3,3a, 4,5,6,6a-hexahydro-2-hydroxy-4-[5'-phenyl-3'(R)-hydroxy-1'-pentyl]-5-(4'-phenyl-benzoyloxy)-2H-cyclopenta[b]furan[compound of the formula (IV)]

A solution of diisobutylaluminum hydride (DIBAL) (9.1 kg) in dry toluene (31 L) was added to a stirred solution of the compound of formula (V) (6.8 kg) in toluene (70 L) at −72°/−80° C., after 1 hour (TLC monitoring) ethyl acetate (5 L) was added, followed by addition of sodium hydrogen sulphate 1M (240 L). The organic layer was separated and dried on sodium sulphate (9 kg), filtered, washed with toluene; AcOEt (5 L:5 L). The water layer was washed with AcOEt (3×35 L). The organic layers were collected and dried with sodium sulphate (9 kg), filtered, washed with toluene: AcOEt 1:1 (40 L). The organic layers were collected and toluene (100 L), triethylamine (0.5 L) were added to stabilize the triol. The solution of the triol was chromatographed on silicagel (34 kg) packed on toluene (60 L), using toluene:AcOEt (1:1) (400 L) and AcOEt (560 L) respectively as eluent,the following fractions in the following order were collected; fraction I (50 L), fractions II and III (400 L) each, fraction IV (230 L). Fraction III was rich of the desired product. The solvent was removed in vacuo. To the residue (20 L) diisopropyl ether (DIPE) (65 L) was added, cooled to 0° C. A solid substance was formed, filtered and washed with DIPE:AcOEt 3:1 (2×10 L) to give a white crystalline product yield (2.8 kg, 63.1%). Any excess of DIBAL was used to remove the PPB while the compound of the formula (V) was reduced to the compound of the formula (IV).

EXAMPLE 9

Preparation of 3,3a,4,5,6,6a-hexahydro-2,5-dihydroxy-4-[5'-phenyl-3'(R)-hydroxy-1'-pentyl]-2H-cyclo-penta[b]furan [compound of the formula (III)]

A mixture containing 3,3a, 4,5,6,6a-hexahydro-2-hydroxy-4-[5'-phenyl-3'(R)-hydroxy-1'-pentyl]-5-(4'-phenyl-benzoyl-oxy)-2H-cyclopenta[b]furan (65.2 g, 133.4 mmol), potassium carbonate (19.0 g, 133.4 mmol) and methanol (330 ml) is stirred at 40°–45° C. for 5 hours, then cooled to 0° C. and the pH value is adjusted to 7-8 by the slow addition of 1 N phosphoric acid solution. After filtering off the precipitate, the filtrate is washed twice with water (70 ml) each and then twice with a 2:1 mixture of methanol (30 ml) and water each.

After adding saline to the filtrate and extracting four times with ethyl acetate (250 ml) each, the combined organic phase is washed with saline, dried and evaporated under reduced pressure. The solid obtained is dissolved in ethyl acetate (100 ml) at 60° C., diisopropyl ether (100 ml) are added to the solution, cooled to room temperature and then hexane (200 ml) are slowly added. After stirring the mixture at 0° C., the crystalline precipitate is filtered, washed twice with a 2:1 mixture of diisopropyl ether (30 ml) and ethyl acetate each and dried to give white crystalline title compound (35.93 g, 87.90%) of formula (III), m.p.: 103°–106° C. $[\alpha]_D = -47°$(c=1, ethyl acetate). IR spectrum (taken on a Zeiss Specord M-80 type spectrometer) (KBr, cm$^{-1}$): 3380 (OH), 3030 (CH aromatic), 2980, 2960, 2920, 2860 (CH aliphatic), 1600, 1590, 1570, 1500 (aromatic ring vibration), 1090 (C—O—C), 1000 [C—O—(H)], 750, 700 (monosubst. aromatic). $^1$H-NMR spectrum (taken on a Bruker WP 80 device, CDCl$_{13}$, TMS standard, δ ppm): 7.23 (s, 5H, aromatic H), 5.64, 5.51 (d, 1H, 3-H),4.63 (m, 1H, 1-H), 3.90 (1H, 7-H), 3.60 (1H, 3'-H).

The product is an 1:1 mixture of the exo and endo isomers.

EXAMPLE 10

Preparation of the compound of the formula (II)

4-carboxybutyl-triphenylphosphonium bromide (147.2 g, 3.32 mmol) and potassium tert-butoxide (186g, 1.66 mmol) are added to a solution of 3,3a, 4,5,6,6a-hexahydro-2,5-dihydroxy-4-[5'-phenyl-3'(R)-hydroxy-1'-pentyl]-2H-cyclopenta [b]furan (33.9 g, 110.7 mmol) [compound of the formula (III)]in tetrahydrofuran (500 ml) and the solution is cooled to −25° C. The mixture is stirred first at −20° C. then at 0° C. altogether 6 hours, then the pH is adjusted to 8–9 by adding 2M aqueous sodium hydrogen sulfate solution and tetrahydrofuran is distilled off under reduced pressure. After adding water (200 ml) to the residue, the mixture is cooled to room temperature, the precipitate is filtered, washed twice with saturated sodium hydrogen carboate solution (200 ml) each and then twice with water (100 ml) each. The combined aqueous phase is washed twice with methylene chloride (150 ml) each, the pH value is adjusted to 3–4 by using sodium hydrogen sulfate solution and then extracted twice with ethyl acetate (500 ml) each. The combined ethyl acetate phase is twice washed with saline (100 ml) each and evaporated. The thick, liquid suspension is shaken with acetone (100 ml) for 10 minutes, the precipitate is filtered, washed 6 times with 100 ml of 40:25 (by volume) mixture of diisopropyl ether and aceton each and the filtrate is evaporated under reduced pressure to obtain the title compound of the formula (II) as an oily residue in a yield of 85%, which can be transformed to the compound of formula (I) without purification.

EXAMPLE 11

Preparation of compound of the formula (II)

To a stirred suspension of 4-carboxybutyl triphenyl phosphonium bromide (5.32 kg) in THF (40 L) under nitrogen at 0°–5° C. potassium butoxide (4.49 kg) was added, and stirred for 20 min. at room temperature. To the resultant red orange solution of ilyde at −15°/−10° C. the compound of the formula (III) was added (1.23 kg) in THF (8 L), the mixture was stirred for 4–7 hours (TLC monitoring). The reaction mixture was diluted with water (25 L), washed with toluene (25 L), the organic phase was separated. The water layer was washed with chloroform (3×6 L), acidified with sodium hydrogen sulfate 2M (15 L), extracted with AcOEt (18 L and 22×6 L) successively. The organic layer was washed with 15% sodium chloride solution (2×6 L), dried on sodium sulphate (0.4 kg), filtered. The precipitate was washed twice with AcOEt (4 L). The solvent was removed in vacuo, the slurry was shaken with DIPE: :acetone 2:1 (18 L) to crystallize the byproduct triphenylphosphoxide which was removed by filtration, washed with DIPE:acetone 1:1 (4×3 L). The organic layer was concentrated in vacuo to give the compound of the formula (II) which is used directly without isolation for the next step.

EXAMPLE 12

Preparation of 13,14-dihydro-15(R)-17-phenyl-18,19,20-trinor-PGF$_{2\alpha}$ isopropyl ester [compound of theformula (I)]

After adding anhydrous potassium carbonate (22.95 g) and isopropyl iodide (37.55 g, 221.4 mmol) to the solution of crude 13,14-dihydro-15(S)-17-phenyl-18,19,20-trinor-PGF$_{2\alpha}$ in 200 ml of dry dimethylformamide (50.64 g, 110.7 mol) obtained in Example 6, the mixture is stirred at 50° C. for 5 hours, then the reaction mixture is poured to a mixture of water (900 ml), 2M sodium hydrogen sulfate solution (120 ml) and ethyl acetate (500 ml).The aqueous phase is extracted with additional ethyl acetate (500 ml).The combined ethyl acetate phase is successively washed twice with 2% lithium chloride solution (500 ml) each, saturated sodium hydrogen carbonate solution (100 ml) and twice with saline (200 ml) each, dried and ethyl acetate is evaporated under reduced pressure. The oily residue is purified by chromatography on silica gel (1 kg) containing silicon gel by using a 20:1 mixture of methylene chloride and isopropanol as eluent, then on silica gel (900 g) by using an 1:1 mixture of ethyl acetate and hexane as eluent to obtain after evaporation colorless oily title compound (16 g) of the formula (I) , R$_f$=0.42 (diisopropyl ether/acetone/water 40:25:1), [α]$_D$= +34° (c=1, acetonitrile) . IR spectrum (taken on a Zeiss Specord M-80 type spectrometer, by using the liquid film method between NaCl sheets) (cm$^{-1}$): 3400 (OH), 3060 (CH aromatic), 2990, 2930, 2860 (CH aliphatic), 1730 (C=O), 1600, 150 (aromatic ring vibration), 1110 (C—O—C), 750, 700 (monosubst. aromatic). $^1$H-NMR spectrum (taken on a Bruker AC 400 device, CDCl$_3$, TMS inner standard, δ ppm):

7.24 (s, 5H, aromatic H), 5.44 (dd, 1H, 6-H), 5.41 (dd, 1H, 5-H), 4.99 (m, 1H, —CH—isopropanol), 4.17 (s, 1H, 9-H), 3.94 (s, 1H, 11-H), 3.66 (m, 1H, 15-H).

EXAMPLE 13

Preparation of 13,14 -dihydro-15(R)17-phenyl-18, 19, 20-trinor PGF$_{2\alpha}$ isopropyl ester [Compound of the general formula (I), wherein R is isopropyl group]

To the crude product of the formula (II) dissolved in DMF (6 L), potassium carbonate (1.24 kg) and isopropyl iodide (1.15 L) were added, and the mixture was warmed to 45°–50° C. over a period of 5–7 hours at which time the reaction was completed (TLC monitoring). The mixture was diluted with water (2.8 L) , acidified to pH 2–3 with sodium hydrogen sulphate 1M (13 L). The water layer was extracted with AcOEt: hexane 3:2 (3×9 L), whereupon the organic layer was washed with water (2×4 L) and dried over sodium sulphate (1.5 kg) filtered. The precipitate was washed with AcOEt (2×5 L), concentrated in vacuo, furnishing the target compound as a light brown oil. The crude oil (2.7 kg) was subjected to a column chromatography twice on silicagel.

The crude oil was dissolved in DIP:acetone 3:1 (6 L) and chromatographed on silicagel (70 kg) using DIPE:acetone 3:1 (1200 L), as eluent, and five fractions were collected in the following order; I (280), II (50), III (10), IV (270) and V (70 L) respectively. Fraction IV was containing the major amount of the product (TLC monitoring) which was concentrated in vacuo. The resulting oil was dissolved in dichloromethane (6 L) and chromatographed on silicagel (20 kg) using a gradient elution with dichloromethane (20 L) and dichloromethane:isopropanol 40:1 (61.5 L), 30:1 (20.7 L) and 5:1 (60 L) successively. Five fractions were collected in the following order; I (127 L), II (0.5 L), III (0.5 L), IV (12 L) and V (5 L) respectively. The purity of the fractions were investigated with TLC and HPLC. Fraction IV was found to be pure. The solvent was removed in vacuo, the yellowish oil was treated with active carbon (0.11kg) in isopropanol (6.2 L) , filtered, washed with isopropanol (2×0.56 L).The solvent was removed in vacuo (0.2 bar) at 40°–50° C. to give the target compound as pure colorless to slightly yellowish oil yield (0.96 kg, 55.5 %).

EXAMPLE 14

Preparation of 3,3a, 4,5,6,6a-hexahydro-2,5-dihydroxy-4-[5'-phenyl-3'-(R)-hydroxy-1'-pentyl)-2H-cyclopenta[b]-furan [compound of the formula (III)]

A solution containing 3,3a, 4,5,6,6a-hexahydro-2-oxo-4-[ 5'-phenyl-3'(R)-hydroxy-1'-pentyl ]-5-(4'-phenylbenzoyloxy- 2H-cyclopenta[b]furan (6.8 g, 14 mmol) in anhydrous toluol (82 ml) is cooled to −80° C. and diisobutyl aluminum hydride (9.1 g, 64 mmol) dissolved in of anhydrous toluene (31 ml) are dropwise added under cooling. The reaction mixture is stirred at a temperature between −70° C. and −80° C. until the reaction becomes complete (about 1 hour). Then, the reaction mixture is poured into 1M sodium hydrogen sulfate solution (204 ml), stirred for 45 minutes and after separating the phases the product remained in the aqueous phase is extracted into ethyl acetate. After combining, the organic phase is dried over anhydrous sodium sulfate and then transferred to a column prepared from silica gel (34 g) and toluene (60 ml). The desired product is eluted with a mixture of toluene and ethyl acetate. The fraction containing the pure product is evaporated to a volume of 20–25 ml and the product is crystallized by using diisopropyl ether (65 ml). The product obtained is washed by a mixture of diisopropyl ether and ethyl acetate to give the title product (2.8 g) of formula (III) ,m.p.: 103°–106° C.

We claim:

1. A process for the preparation of a compound of the Formula (I)

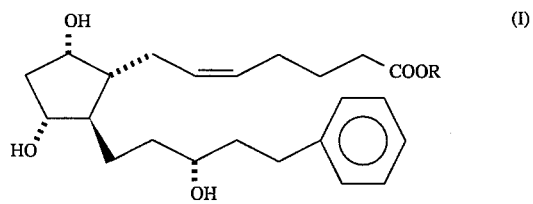

wherein R is a saturated or unsaturated straight branched or cyclic C$_1$ to C$_7$ alkyl, phenyl or benzyl group, which comprises the steps of:

(a) selectively reducing a compound of the Formula (VII)

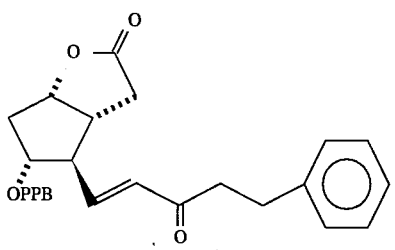

(VII)

wherein PPB stands for 4'-phenylbenzoyl, using lithium tri(secbutyl)borohydride or sodium borohydride to reduce the oxo group on the side chain of the compound of the Formula (VII) to yield a mixture containing a compound of the Formula (VI):

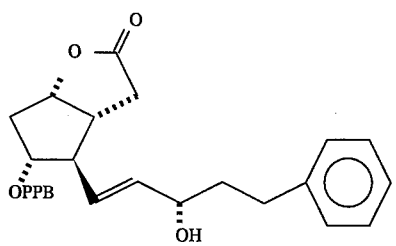

(VI)

(b) chromatographically separating the compound of the Formula (VI) from the mixture formed during step (a) to obtain the compound of the Formula (VI) having the following physical characteristics: m.p. 129° to 130° C., $[\alpha]=-108°$ (C=1, ethylacetate;

(c) hydrogenating the compound of the Formula (VI) step (b) in the presence of a hydrogenation catalyst and a base or a sodium salt to yield a compound of the Formula (V)

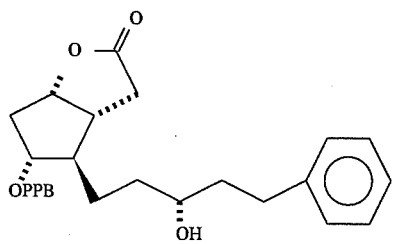

(V)

having an IR spectrum (taken on a Zeiss Specord M-80 type spectrometer) KBr, cm$^{-1}$: 3500 (OH), 3080, 3020 (CH aromatic), 2940, 2860 (CH aliphatic), 1770, 1710 (c=o), 1610, 1500 (aromatic ring vibration), 1290, 1190, 1100 (c—o—c), 850 (p-subst. aromatic), 750, 700 (monoubst. aromatic);

(d) reducing the compound of the Formula (V) using diisobutylaluminum hydride to obtain a compound of the Formula (IV)

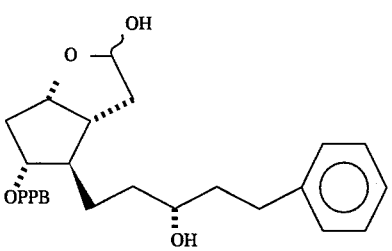

(IV)

(e) removing the 4'-phenyl-benzoyl protecting group from the compound of the Formula (IV) by using a mixture of potassium carbonate and methanol to yield a compound of the Formula (III)

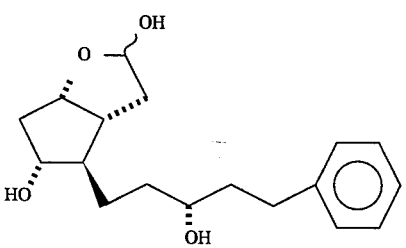

(III)

having the following physical characteristics melting point 103° to 106° C., $[\alpha]_D=-47°$ (C=1, ethyl acetate), and the following spectral data:

IR spectrum (taken on a Zeiss Specord M-80 type spectrometer) (KBr cm$^{-1}$: 3380 (OH), 3030 (CH aromatic), 2980 2960, 2920, 2860 (CH aliphatic) 1600, 1590, 1570, 1500 (aromatic ring vibration), 1090 (c—o—c), 1000 [c—o—(H)], 750, 700 (monosubst. aromatic) $^1$H-NMR spectrum (taken on a Bruker WP 80 device, CDCl$_3$, TMS standard, δ ppm): 7.23 (s, 5H, aromatic H), 5.64, 5.51 (d,1H,3-H), 4.63 (m, 1H, 1-H), 3.90 (1H,7-H), 3.60 (1H, 3'-H) :

(f) reacting the compound of the Formula (III) with 4-carboxybutyl-triphenyl-phosphonium bromide in the presence of potassium tert-butoxide in an ether-type solvent to obtain a compound of the Formula (II)

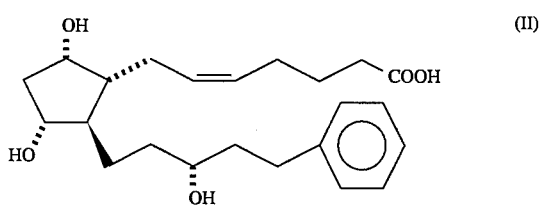

(II)

and;

(g) esterifying the compound of the Formula (II) with a compound of the Formula

R—X wherein X is halogen, sulfate, mesyl, or tosyl, in the presence of potassium carbonate in an organic solvent to obtain the compound of the Formula (I).

2. The process defined in claim 1, step (c), which comprises hydrogenating the compound of the Formula (VI) in the presence of a palladium-on-carbon catalyst.

3. The process defined in claim 1, step (c), which comprises hydrogenating the compound of the Formula (VI) in the presence of sodium salts.

4. The process defined in claim 1, step (g), which comprises esterifying the compound of the Formula (II) with isopropyl iodide in the presence of potassium carbonate in an organic solvent.

5. The process defined in claim 1, which comprises isolating the compounds of Formulae (VI), (V), and (III) in the course of the synthesis starting from the compound of the Formula (VII) and, if desired, purifying them by recrystallization.

6. 3,3a,4,5,6,6a-hexahydro-2,5-dihydroxy-4-[5'-phenyl-3'(R)-hydroxy-1'-pentyl]-2H-cyclopenta[b]furan of the formula (III).

7. 3,3a, 4,5,6,6a-hexahydro-2-oxo-4-[5'-phenyl-3'(R)-hydroxy-1'-pentyl]-5-(4-phenylbenzoyloxy) -2H-cyclopenta[b]furan of the formula (V).

8. A compound of the Formula (IV)

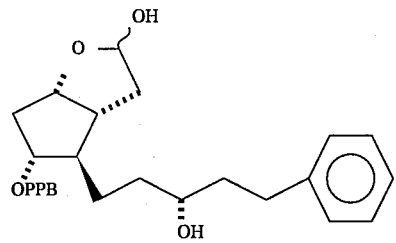

\* \* \* \* \*